US00PP25511P2

(12) United States Plant Patent
Fischer-Toehl

(10) Patent No.: US PP25,511 P2
(45) Date of Patent: May 5, 2015

(54) GERANIUM PLANT NAMED 'TOSFANCRIZ'

(50) Latin Name: *Pelargonium×hortorum*
Varietal Denomination: Tosfancriz

(71) Applicant: Ball Horticultural Company, West Chicago, IL (US)

(72) Inventor: Ilse Fischer-Toehl, Kirchlinteln (DE)

(73) Assignee: Ball Horticultural Company, West Chicago, IL (US)

( * ) Notice: Subject to any disclaimer, the term of this patent is extended or adjusted under 35 U.S.C. 154(b) by 83 days.

(21) Appl. No.: 13/998,055

(22) Filed: Sep. 26, 2013

(51) Int. Cl.
*A01H 5/02* (2006.01)

(52) U.S. Cl.
USPC ..... Plt./325

(58) Field of Classification Search
CPC ..... A01H 5/0277; A01H 5/02; A01H 5/00
USPC ..... Plt./325, 330, 328
See application file for complete search history.

*Primary Examiner* — Kent L Bell
(74) *Attorney, Agent, or Firm* — Audrey Charles

(57) ABSTRACT

A new and distinct cultivar of Geranium plant named 'Tosfancriz', characterized by its semi-double type, red and hot pink bicolored flowers, dark green-colored foliage having zonation, and moderately vigorous, upright-mounded growth habit, is disclosed.

1 Drawing Sheet

Latin name of genus and species of plant claimed: *Pelargonium×hortorum.*

Variety denomination: 'Tosfancriz'.

BACKGROUND OF THE INVENTION

The present invention relates to a new and distinct cultivar of Geranium plant botanically known as *Pelargonium×hortorum* and hereinafter referred to by the cultivar name 'Tosfancriz'.

The new cultivar originated in a controlled breeding program in Weener-Halte, Germany during July 2006. The objective of the breeding program was the development of Geranium cultivars that flower uniformly and have large flowers, dark green-colored foliage, and a moderately vigorous, upright-mounded growth habit.

The new Geranium cultivar is the result of cross-pollination. The female (seed) parent of the new cultivar is Presto Extreme Rose 'Sil Hero', not patented, characterized by its semi-double type, dark rose and pink bicolored flowers, dark green-colored foliage, low growth vigor, and upright-mounded growth habit. The male (pollen) parent of the new cultivar is Fantasia Dark Red 'Sil Magnus', not patented, characterized by its double-type, dark red-colored flowers, dark green-colored foliage having zonation, and vigorous, upright-mounded growth habit. The new cultivar was discovered and selected as a single flowering plant within the progeny of the above stated cross-pollination during June 2007 in a controlled environment in Weener-Halte, Germany.

Asexual reproduction of the new cultivar by terminal stem cuttings since June 2007 in Weener-Halte, Germany and Arroyo Grande, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Tosfancriz' as a new and distinct cultivar of Geranium plant:

1. Semi-double type, red and hot pink bicolored flowers;
2. Dark green-colored foliage having zonation; and
3. Moderately vigorous, upright-mounded growth habit.

Plants of the new cultivar differ from plants of the female parent primarily in leaf zonation and growth vigor. Plants of the new cultivar differ from plants of the male parent primarily in flower type, flower color, and growth vigor.

Of the many commercially available Geranium cultivars, the most similar in comparison to the new cultivar is Savannah Merlot Sizzle 'Duesamesiz', Not patented. However, in side by side comparisons, plants of the new cultivar differ from plants of 'Duesamesiz' in at least the following characteristics:

1. Plants of the new cultivar have petals with more red and less hot pink coloration than plants of 'Duesamesiz'; and
2. Plants of the new cultivar have heavier leaf zonation than plants of 'Duesamesiz'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Tosfancriz'. The plants were grown in 4.5-inch pots for 10 weeks in a greenhouse in West Chicago, Ill.

DETAILED BOTANICAL DESCRIPTION

Figure 1:
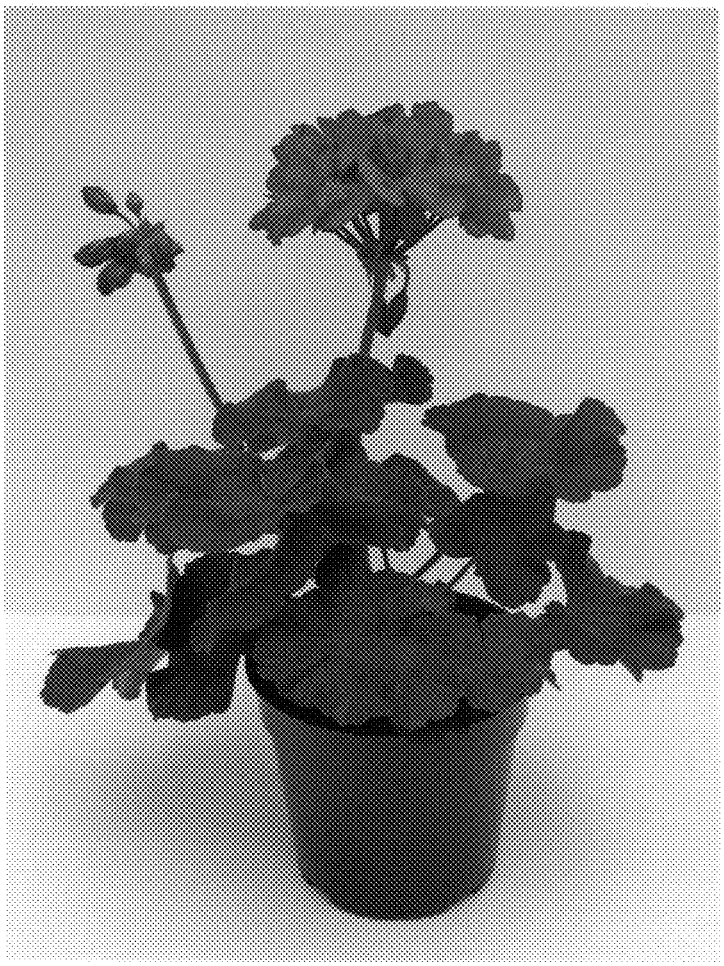
FIG. 1 illustrates a side view of the overall growth and flowering habit of 'Tosfancriz'.
Figure 2:
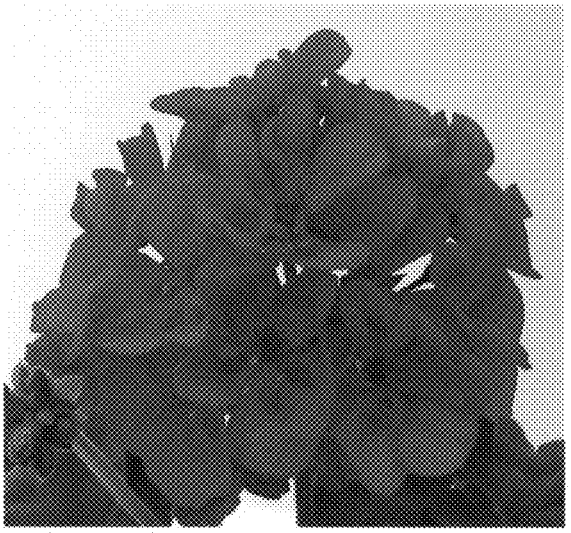
FIG. 2 illustrates a close-up view of an individual umbel of 'Tosfancriz'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in July 2013 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4.5-inch pots for 10 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Pelargonium×hortorum* cultivar Tosfancriz.

Parentage:

*Female parent*.—Presto Extreme Rose 'Sil Hero', not patented.

*Male parent*.—Fantasia Dark Red 'Sil Magnus', not patented.

Propagation:

*Type cutting*.—Terminal stem.

*Time to initiate roots*.—Approximately 9 to 12 days.

*Time to produce a rooted cutting*.—Approximately 24 to 28 days.

*Root description*.—Fibrous.

*Rooting habit*.—Freely branching.

Plant description:

*Commercial crop time*.—Approximately 8 to 9 weeks from a rooted cutting to finish in a 10 cm pot.

*Growth habit and general appearance*.—Moderately vigorous, upright-mounded.

*Size*.—Height from soil level to top of plant plane: Approximately 21.0 cm. Height from soil level to top of foliage: Approximately 10.5 cm. Width: Approximately 19.5 cm.

*Branching habit*.—Freely basal branching, pinching enhances basal branching. Quantity of main branches per plant: Approximately 1.

*Branch*.—Strength: Strong. Length: Approximately 7.5 cm. Diameter: Approximately 7.0 mm. Length of central internode: Approximately 1.1 cm. Texture: Densely pubescent with a mixture of glandular and nonglandular hairs. Gland color: Mixture of 25D and colorless, transparent. Color of young and mature stems: 146B.

Foliage description:

*General description*.—Quantity of leaves per branch: Approximately 8. Fragrance: Slight. Form: Simple. Arrangement: Opposite.

*Leaves*.—Aspect: Petiole is at an acute angle to stem, blade is perpendicular to stem. Shape: Reniform. Margin: Bicrenate, palmately lobed, somewhat wavy. Apex: Obtuse. Base: Cordate. Venation pattern: Palmate. Length of mature leaf: Approximately 8.1 cm. Width of mature leaf: Approximately 9.3 cm. Texture of upper and lower surfaces: Densely pubescent with a mixture of glandular and nonglandular hairs. Gland color: Mixture of 25D and colorless, transparent. Color of upper surface of young foliage: 137A with zonation of N187A and venation of 146B. Color of lower surface of young and mature foliage: Closest to 147B with venation of 146C. Color of upper surface of mature foliage: Darker than 137A with zonation of N187A and venation of 146A.

*Petiole*.—Length: Approximately 5.7 cm. Diameter: Approximately 3.0 mm. Texture: Densely pubescent with a mixture of glandular and nonglandular hairs. Gland color: Mixture of 25D and colorless, transparent. Color: 146A to 146B.

Flowering description:

*Flowering habit*.—'Tosfancriz' is freely flowering under outdoor growing conditions with substantially continuous blooming from spring through autumn and year-round in greenhouse environment.

*Lastingness of individual flower on the plant*.—Approximately 12 to 14 days.

Inflorescence description:

*General description*.—Type: Umbel, semi-spherical. Positioned above foliage. Quantity of fully open umbels per plant: Approximately 1. Quantity of developing umbels per plant: Approximately: 1. Fragrance: Slight. Length or height: Approximately 6.0 cm. Width: Approximately 9.5 cm. Quantity of fully open flowers per inflorescence: Approximately 14.

*Peduncle*.—Strength: Strong. Aspect: Erect. Length: Approximately 11.5 cm. Diameter: Approximately 4.0 mm. Texture: Densely pubescent with a mixture of glandular and nonglandular hairs. Gland color: Mixture of 25D and colorless, transparent. Color: 146A to 146B with an irregular overlay of 187A.

Flower description:

*General description*.—Type: Semi-double.

*Bud*.—Rate of opening: Generally takes 3 to 4 days for bud to progress from first color to fully open flower.

*Bud just before opening*.—Shape: Elliptic. Length: Approximately 1.3 cm. Width: Approximately 7.0 mm. Sepal texture: Densely pubescent with a mixture of glandular and nonglandular hairs. Gland color: Mixture of 25D and colorless, transparent. Petal texture: Glabrous. Petal color: Closest to 71B.

*Corolla*.—Shape: Round. Diameter: Approximately 4.5 cm. Depth: Approximately 2.0 cm.

*Petals*.—Quantity: Approximately 6 petals and 1 to 2 irregularly-shaped petaloids per flower. Shape: Obovate. Appearance: Iridescent. Margin: Entire. Apex: Obtuse. Base: Attenuate. Length of upper petals: Approximately 2.7 cm. Width of upper petals: Approximately 1.9 cm. Length of lower petals: Approximately 2.4 cm. Width of lower petals: Approximately 2.1 cm. Texture of upper and lower surfaces: Glabrous. Color of upper surface of upper petals when fully open: 45A tinged with N74A, central lateral stripe of 53A, and venation of 53A at base. Color of lower surface of upper petals when fully open: Closest to 46B with venation of 53A. Color of upper surface of lower petals when fully open: N74A with an overlay of 45A and central spot of 53A. Color of lower surface of lower petals when fully open: N74B tinged with 46B.

*Calyx*.—Shape: 5-pointed star. Diameter: Approximately 2.3 cm.

*Sepals*.—Quantity per flower: Approximately 5, fused at base. Shape: Lanceolate. Margin: Entire. Apex: Acuminate. Length of upper sepal: Approximately 1.2 cm. Width of upper sepal: Approximately 5.0 mm. Length of lower sepals: Approximately 1.2 cm. Width of lower sepals: Approximately 2.0 mm. Texture of upper surface: Glabrous. Texture of lower surface: Densely pubescent with a mixture of glandular and nonglandular hairs. Gland color: Mixture of 25D and colorless, transparent. Color of upper surface: 144A. Color of lower surface: 144A with streaks of 187C near base.

*Pedicel*.—Strength: Strong. Aspect: Acute angle to peduncle. Length: Approximately 2.4 cm. Diameter: Approximately 1.5 mm. Texture: Densely pubescent with a mixture of glandular and nonglandular hairs. Gland color: Mixture of 25D and colorless, transparent. Color: 144A with a heavy overlay of 187C.

*Reproductive organs*.—Androecium: Quantity of mature stamens: Approximately 8 per flower. Anther shape: Oblong. Anther length: Approximately 2.0 mm. Anther color: 64B. Filament length: Approximately 7.0 mm. Filament color: NN155D with an overlay of 64D nearest anther. Pollen amount: Moderate. Pollen color: 32A. Gynoecium: Pistil quantity: 1 per flower. Pistil length: Approximately 8.0 mm. Stigma shape: 5 branched. Stigma length: Approximately 2.0 mm. Stigma color: 53A. Style length: Approximately 2.0 mm. Style color: 53B. Ovary length: Approximately 4.0 mm. Ovary texture: Densely pubescent. Ovary color: 145A.

Seed and fruit production: Neither seed nor fruit production has been observed.

Disease and pest resistance: Resistance to pathogens and pests common to Geranium has not been observed.

What is claimed is:

1. A new and distinct cultivar of Geranium plant named 'Tosfancriz', substantially as herein illustrated and described.

* * * * *